United States Patent [19]

Turner

[11] Patent Number: 4,708,865

[45] Date of Patent: Nov. 24, 1987

[54] METHOD AND COMPOSITION FOR ARTIFICIALLY TANNING THE HUMAN EPIDERMIS

[76] Inventor: Janet N. Turner, Route Box 195, Warsaw, MO.

[21] Appl. No.: 898,645

[22] Filed: Aug. 21, 1986

[51] Int. Cl.$^4$ .............................................. A61K 7/42
[52] U.S. Cl. ...................................... 424/59; 424/60; 424/63
[58] Field of Search ................ 424/59, 60, 63; 8/405, 8/406, 424

[56] References Cited

U.S. PATENT DOCUMENTS

| | | | |
|---|---|---|---|
| 1,108,157 | 8/1914 | Ernst | 8/424 |
| 2,944,869 | 7/1960 | Kalopissis et al. | 8/424 |
| 2,948,658 | 8/1960 | Green | 195/43 |
| 2,949,403 | 8/1960 | Andreadis et al. | 424/59 |
| 3,177,120 | 4/1965 | Black et al. | 424/59 |
| 3,184,388 | 5/1965 | Kalopissis | 424/59 |
| 3,993,436 | 11/1976 | Fujinuma | 8/424 |
| 4,217,344 | 8/1980 | Vanlerberghe et al. | 252/31.6 |

FOREIGN PATENT DOCUMENTS 487239  6/1938  United Kingdom ................ 8/406

OTHER PUBLICATIONS

Redgrove et al., Hair-Dyes and Hair-Dying Chemistry and Technique, 1939, pp. 46 to 50, 59 to 64 to 68.
Weissberger Abstract, O. G. 11/6/51, vol. 652, pp. 289–290.
Today's Health, 1964, vol. 48, No. 8, pp. 14 to 17, 68, 70 and 71.
Bennett, The Cosmetic Formulary, 1937, p. 127.
Drug & Specialty Formulas, 1941, Belanger, pp. 117 & 118.

*Primary Examiner*—Dale R. Ore
*Attorney, Agent, or Firm*—Robert B. Stevenson

[57] ABSTRACT

A solution for tanning human skin comprising essentially equal volumes of aged (e.g., 12 hours) filtered mixtures of 4 wt. % cutch powder (catechu), 4 wt. % logwood powder and 6 wt. % walnut powder dissolved in 1 part by volume alcohol (e.g., isopropyl alcohol), 2 parts by volume water (distilled), and 2 parts by volume 4 wt. % $AlK(SO_4)_2$ in 0.8 wt. % saline solution and an equal volume of hydroxyaceton solution consisting of for every 1 part by volume alcohol (e.g., IPA), 2 parts by volume of 5 wt. % sorbitol in water (distilled) and sufficient dihydroxyacetone to make the final tanning solution from about 3 to about 10 wt. % dihydroxyacetone. Such a solution produces a warm, uniformly dark, natural appearing tan artificially even when used on fair skinned humans.

6 Claims, No Drawings

METHOD AND COMPOSITION FOR ARTIFICIALLY TANNING THE HUMAN EPIDERMIS

BACKGROUND OF THE INVENTION

1. Field of the Invention

This invention relates to a cosmetic composition. More specifically, the invention relates to an improved composition for producing an artificial tanning effect when topically applied to human skin.

2. Description of the Prior Art

It is generally known that dihydroxyacetone and certain closely related compounds (see U.S. Pat. Nos. 2,949,493 and 3,184,388) when administered topically to human skin will produce a temporary tanning effect reminiscent of prolonged exposure to the sun's rays. It is also generally known that dihydroxyacetone products have very short shelf lives, thus various additives such as salicylates and cinnamates (see U.S. Pat. No. 3,177,120) have been proposed to extend shelf life and improve the skin coloring effect. The use of dihydroxyacetone also results in an undesirable orange cast or hue when applied to particularly fair skinned humans.

SUMMARY OF THE INVENTION

In view of the problems associated with previous methods of using dihydroxyacetone as an artificial tanning agent, the present invention provides an improved formulation and composition that avoids the previous short shelf life problems and also produces a warm, uniform dark natural appearing tan artificially even on fair skinned humans. Thus, the present invention produces an improved topical solution for artificially tanning the human skin comprising a blend of essentially equal volumes of filtered mixtures of:

(a) a cutch powder containing mixture consisting of for every 1 part by volume alcohol, about 2 parts by volume water and about 2 parts by volume of 4 wt. % $AlK(SO_4)_2$ dissolved in 0.85 wt. % saline solution to which has been added at least 4 grams of cutch powder per 100 parts total volume;

(b) a logwood powder containing mixture consisting of for every 1 part by volume alcohol, about 2 parts by volume water and about 2 parts by volume of 4 wt. % $AlK(SO_4)_2$ dissolved in 0.8 wt. % saline solution to which has been added at least 4 grams of logwood powder per 100 parts total volume; and (c) a walnut powder containing mixture consisting of for every 1 part by volume alcohol, about 2 parts by volume water and about 2 parts by volume of 4 wt. % $AlK(SO_4)_2$ dissolved in 0.85 wt. % saline solution to which has been added at least 6 grams of walnut powder per 100 parts total volume, and an equal volume of a solution consisting of for every 1 part by volume alcohol, about 2 parts by volume of 5 wt. % sorbitol dissolved in water and sufficient dihydroxyacetone to produce at least a 3 wt. % up to about 10 wt. % final concentration in the resulting topical solution.

It is a primary object of the present invention to provide an artificial tanning solution that employs a combination of naturally occurring dye substances in association with dihydroxyacetone to alleviate and improve the otherwise orange case or hue previously produced by the use of dihydroxyacetone particularly on fair skinned humans. It is a further object of the present invention to provide an artificial tanning solution that produces a uniformaly dark tanning effect. Fulfillment of these objects and the presence and fulfillment of additional objects will become apparent upon complete reading of the specification and claims.

DESCRIPTION OF THE PREFERRED EMBODIMENTS

The improved artificial tanning cosmetic formuation according to the present invention employs the known artificial tanning agent dihydroxyacetone, preferably at overall concentration of about 3 to 10 wt. %, along with a novel combination of naturally occurring dyes or coloring agents. The improved formulation imparts a cosmetic color to the skin lasting from about 4 to 6 days or even longer. Because of the presence of the novel combination of other natural occurring coloring agents, the tendency for the dihydroxyacetone to produce an orange tone is virtually eliminated, resulting in an even, dark brown coloring effect reminiscent of prolonged exposure to the sun.

In selecting the natural dyes to complement the dihydroxyacetone, many materials occurring naturally such as willow, tea, coffee, blackberry, cherry, polkberry and the like were tested and screened for compatibility and beneficial effect, but were found to be ineffective or otherwise undesirable. In preparing the complementary dyes, it was found that the intentional removal or separation of the protein fraction of the naturally occurring powder material was appropriate for purposes of this invention. Preferably, this is accomplished by precipitating the protein fraction of the natural dyestuff from a solution by using various salts, such as aluminum potassium sulphate ($AlK(SO_4)_2$; alum) or the like. Typically, a 3 to 8 wt. % $AlK(SO_4)_2$ solution is used to precipitate the protein fraction from an alcohol/water solution to which the powdered natural dye has been added. Preferably, a 5 wt. % $AlK(SO_4)_2$ solution is employed with sufficient standing (e.g., 12 hours or more) to effect the precipitation of the protein fraction. Optionally, a liquid fraction can be removed from the natural dye component prior to formulation into the final desired cosmetic solution, but such step is felt to be unnecessary for purposes of this invention.

The actual preparation of the complementary dye component according to the present invention generally involves mixing a powdered plant product with sufficient alcohol and water to achieve complete dissolution of the powder. Typically, any conventional alcohol generally used in the cosmetic industry can be employed such as ethanol, isopropyl alcohol or the like. Preferably, isopropyl alcohol is to be employed because of its germicidal properties and compatibility with the skin. Typically, a 20 volume % alcohol solution is required to conveniently dissolve the powdered material products. Concentrations above 20 volume % are felt unnecessary unless a true solution cannot be achieved at the lower concentration. Preferably, the solution used to dissolve the powdered natural products (the complementary dye) is a water/alcohol mixture containing $AlK(SO_4)_2$ and/or other salts used to precipitate the protein fraction. Typically, a 2 wt. % concentration of the salt is sufficient to achieve the desired protein separation without deleteriously effecting the final cosmetic formulation. One particularly convenient method preparing the complementary dye component for use in the final cosmetic formulation is to dissolve the powdered plant product in a mixture consisting of for every 1 part by volume alcohol, 2 parts by volume water and 2 parts by volume of a 5 wt. % AlK(SO$_4$)$_2$ in a 0.8 wt. % saline solution. Conveniently, this solution is allowed to stand until the protein fraction precipitates (preferably, at least 12 hours) and is then filtered to remove all sediment. It should be appreciated that various other techniques as generally known in the art can be employed to achieve the protein fraction separation and removal and as such are considered equivalent for purposes of this invention.

The particular combination of naturally occurring plant products that have been found to be effective according to the present invention involves three plant products each of which contributes a complementary tone or hue to the orange cast associated with the use of dihydroxyacetone. In particular, logwood powder (hematoxylon) contributes a blue cast, cutch powder (catechu) contributes a red cast and walnut powder contributes a green cast. The combination of the three when used with dihydroxyacetone has been found to produce a warm, even, dark brown coloration on human skin, even if the skin is relatively light (fair) in color.

Preferably, the three component dyes are individually prepared as separate solutions (typically, at least 4 wt. % solutions of a natural powder in alcohol/water solution with alum). These individual solutions are filtered or otherwise treated such as to remove the undesirable protein fraction or component. Thus, for purposes of this invention, the description of the individual solutions as being filtered encompasses other methods of removing the protein fraction.

Having prepared the three individual component dye solutions, they are then blended or mixed together along with a fourth solution containing sufficient dihydroxyacetone to achieve a final concentration of about 3 to about 10 wt. % dihydroxyacetone. It has been discovered that by starting with equal volumes of individual filtered solutions originally prepared containing at least 4 wt. % of the complementary dye's cutch and logwood powders, respectively, and at least 6 wt. % of walnut powder and adding (diluting) these three equal volumes with another equal volume of a fourth solution containing sufficient dihydroxyacetone to achieve the overall concentration range of 3 to 10 wt. % dihydroxyacetone, a particularly effective artificial tanning formulation will be achieved.

The fourth component solution containing the dihydroxyacetone can be generally any solution containing sufficient dihydroxyacetone to achieve the desired final overall concentration and still be compatible with the other complementary dye solutions. As such, the use of the same or similar solvent system is preferred. Preferably, sorbitol is added to the fourth solution as a humectant. Typically, a 3 to about 10 wt. % solution of sorbitol is employed. Preferably, a 5 wt. % sorbitol is effective, while above 5 wt. % a tendency to produce a sticky feeling when applied to the skin may be observed. Consequently, the fourth solution according to the present invention contains for every 1 part by volume alcohol about 2 parts by volume of 5 wt. % sorbitol dissolved in water and sufficient dihydroxyacetone to produce at least a 3 wt. % solution in the final four component cosmetic tanning solution. When using the four component system method to prepare the final cosmetic artificial tanning solution, one merely adds equal volumes of the respective individual complementary dye solutions to a similar amount of the dihydroxyacetone containing fourth solution. The following Example is presented to further illustrate a composition of the preferred embodiment according to the present invention and how it is produced.

EXAMPLE

To a mixture of 20 cc of isopropyl alcohol, 40 cc of distilled water and 40 cc of 4 wt. % AlK(SO$_4$)$_2$ dissolved in 0.85 saline solution was added 4 grams cutch powder. The cutch mixture was then allowed to set for 12 hours after which the solution was filtered and 90 cc of cutch containing filtrate was recovered.

To a mixture of 20 cc of isopropyl alcohol, 40 cc of distilled water and 40 cc of 4 wt. % AlK(SO$_4$)$_2$ dissolved in 0.85 saline solution was added 4 grams logwood powder. The logwood mixture was then allowed to set for 12 hours after which the solution was filtered and 80 cc of logwood filtrate was recovered.

To a mixture of 20 cc of isopropyl alcohol, 40 cc of distilled water and 40 cc of 4 wt. % AlK(SO$_4$)$_2$ dissolved in 0.85 saline solution was added 6 grams walnut powder. The walnut mixture was then allowed to set for 12 hours after which the solution was filtered and 70 cc of walnut filtrate was recovered.

To a mixture of 10 cc of isopropyl alcohol and 20 cc of 5 wt. % sorbitol dissolved in distilled water was added 3.6 grams of dihydroxyacetone. To this dihydroxyacetone solution was added 30 cc of the cutch containing filtrate, 30 cc of the logwood containing filtrate and 30 cc of the walnut containing filtrate. The resulting 3 wt. % dihydroxyacetone solution produced an even, dark brown artificial tan when applied topically to human skin.

Having thus described the invention with a certain degree of particularity, it is manifest that many changes may be made in the details without departing from the spirit and scope of this disclosure. It is understood that the invention is not limited to the exemplified embodiment set forth herein but is to be limited only by the scope of the attached claims, including the full range of equivalents to which each element thereof is entitled.

I claim:

1. A topical solution for artificially tanning the human skin comprising a blend of essentially equal volumes of filtered mixtures of:
   (a) a cutch powder containing mixture consisting of for every 1 part by volume alcohol, about 2 parts by volume water and about 2 parts by volume of 4 wt. % AlK(SO$_4$)$_2$ dissolved in 0.85 wt. % saline solution to which has been added at least 4 grams of cutch powder per 100 parts total volume;
   (b) a logwood powder containing mixture consisting of for every 1 part by volume alcohol, about 2 parts by volume water and about 2 parts by volume of 4 wt. % AlK(SO$_4$)$_2$ dissolved in 0.8 wt. % saline solution to which has been added at least 4 grams of logwood powder per 100 parts total volume; and
   (c) a walnut powder containing mixture consisting of for every 1 part by volume alcohol, about 2 parts by volume water and about 2 parts by volume of 4 wt. % AlK(SO$_4$)$_2$ dissolved in 0.85 wt. % saline solution to which has been added at least 6 grams of walnut powder per 100 parts total volume, and an equal volume of a solution consisting of for every 1 part by volume alcohol, about 2 parts by volume of 5 wt. % sorbitol dissolved in water and sufficient dihydroxyacetone to produce at least a 3 wt. % up to about 10 wt. % final concentration in said resulting topical solution.

2. A topical solution of claim 1 wherein said alcohol is isopropyl alcohol.

3. A topical solution of claim 2 wherein said dihydroxyacetone is present in said final topical solution at a concentration of about 3 wt. %.

4. A method of artificially tanning the human skin consisting of the step of topically applying an effective amount of a solution comprising a blend of essentially equal volumes of filtered mixtures of:
   (a) a cutch powder containing mixture consisting of for every 1 part by volume alcohol, about 2 parts by volume water and about 2 parts by volume of 4 wt. % $AlK(SO_4)_2$ dissolved in 0.85 wt. % saline solution to which has been added at least 4 grams of cutch powder per 100 parts total volume;
   (b) a logwood powder containing mixture consisting of for every 1 part by volume alcohol, about 2 parts by volume water and about 2 parts by volume of 4 wt. % $AlK(SO_4)_2$ dissolved in 0.8 wt. % saline solution to which has been added at least 4 grams of logwood powder per 100 parts total volume; and
   (c) a walnut powder containing mixture consisting of for every 1 part by volume alcohol, about 2 parts by volume water and about 2 parts by volume of 4 wt. % $AlK(SO_4)_2$ dissolved in 0.85 wt. % saline solution to which has been added at least 6 grams of walnut powder per 100 parts total volume, and an equal volume of a solution consisting of for every 1 part by volume alcohol, about 2 parts by volume of 5 wt. sorbitol dissolved in water and sufficient dihydroxyacetone to produce at least a 3 wt. % up to about 10 wt. % final concentration in said resulting topical solution.

5. A method of claim 4 wherein said alcohol is isopropyl alcohol.

6. A method of claim 5 wherein said dihydroxyacetone is present in said final topical solution at a concentration of about 3 wt. %.

* * * * *